(12) United States Patent
Lee et al.

(10) Patent No.: US 12,106,955 B2
(45) Date of Patent: Oct. 1, 2024

(54) EXCIMER LAMP ELECTRODE GEOMETRY

(71) Applicant: GOODRICH CORPORATION, Charlotte, NC (US)

(72) Inventors: Yongduk Lee, Vernon, CT (US); Matthew Robert Pearson, Hartford, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 289 days.

(21) Appl. No.: 17/506,116

(22) Filed: Oct. 20, 2021

(65) Prior Publication Data
US 2023/0120509 A1  Apr. 20, 2023

(51) Int. Cl.
| | |
|---|---|
| H01J 61/06 | (2006.01) |
| A61L 2/10 | (2006.01) |
| B64D 11/00 | (2006.01) |
| H01J 61/12 | (2006.01) |

(52) U.S. Cl.
CPC ............... *H01J 61/06* (2013.01); *A61L 2/10* (2013.01); *B64D 11/00* (2013.01); *H01J 61/12* (2013.01); *A61L 2202/11* (2013.01); *A61L 2202/25* (2013.01)

(58) Field of Classification Search
CPC ........ H01J 61/06; H01J 61/0672; H01J 61/12; H01J 61/125; H01J 61/16; H01J 65/046; A61L 2/00; A61L 2/10; A61L 2202/11; A61L 2202/25

See application file for complete search history.

(56) References Cited

U.S. PATENT DOCUMENTS

| | | | |
|---|---|---|---|
| 8,344,627 B1 | 1/2013 | Hooke et al. | |
| 8,460,283 B1 | 6/2013 | Laroussi et al. | |
| 11,004,660 B2 | 5/2021 | Prager et al. | |
| 2008/0199354 A1* | 8/2008 | Gordon | ..................... A61L 2/10 |
| | | | 422/186.3 |
| 2009/0295288 A1 | 12/2009 | Eden et al. | |
| 2011/0095684 A1* | 4/2011 | Moriyasu | .............. H01J 61/363 |
| | | | 313/637 |
| 2017/0186596 A1 | 6/2017 | Shinoda et al. | |

(Continued)

FOREIGN PATENT DOCUMENTS

| | | |
|---|---|---|
| CN | 106900135 | 6/2017 |
| CN | 108093551 | 3/2020 |

(Continued)

OTHER PUBLICATIONS

European Patent Office, European Search Report dated Jul. 13, 2023 in Application No. 22201153.8.

*Primary Examiner* — Thai Pham
(74) *Attorney, Agent, or Firm* — SNELL & WILMER L.L.P.

(57) ABSTRACT

An excimer lamp includes a plurality of arc tubes and an electrode pair. The electrode pair comprises a plurality of elongated electrode plates extending along a tube axis direction of the plurality of arc tubes. Each electrode plate comprises a polarity opposite that of an adjacent electrode plate (i.e., alternating polarities). The plurality of arc tubes and the plurality of electrode plates are disposed in an alternating side-by-side orientation such that an arc tube of the plurality of arc tubes is disposed between adjacent electrode plates of the plurality of electrode plates.

19 Claims, 6 Drawing Sheets

(56) References Cited

U.S. PATENT DOCUMENTS

2019/0096656 A1\* 3/2019 Do .................. H01J 65/044
2022/0184249 A1\* 6/2022 Childress .................. A61L 2/10

FOREIGN PATENT DOCUMENTS

| CN | 111697869 | | 9/2020 |
| JP | 2010020979 | | 1/2010 |
| JP | 2010020979 A | \* | 1/2010 |
| JP | 2019149231 A | \* | 9/2019 |
| KR | 20200091167 | | 7/2020 |
| WO | 2004054327 | | 6/2004 |

\* cited by examiner

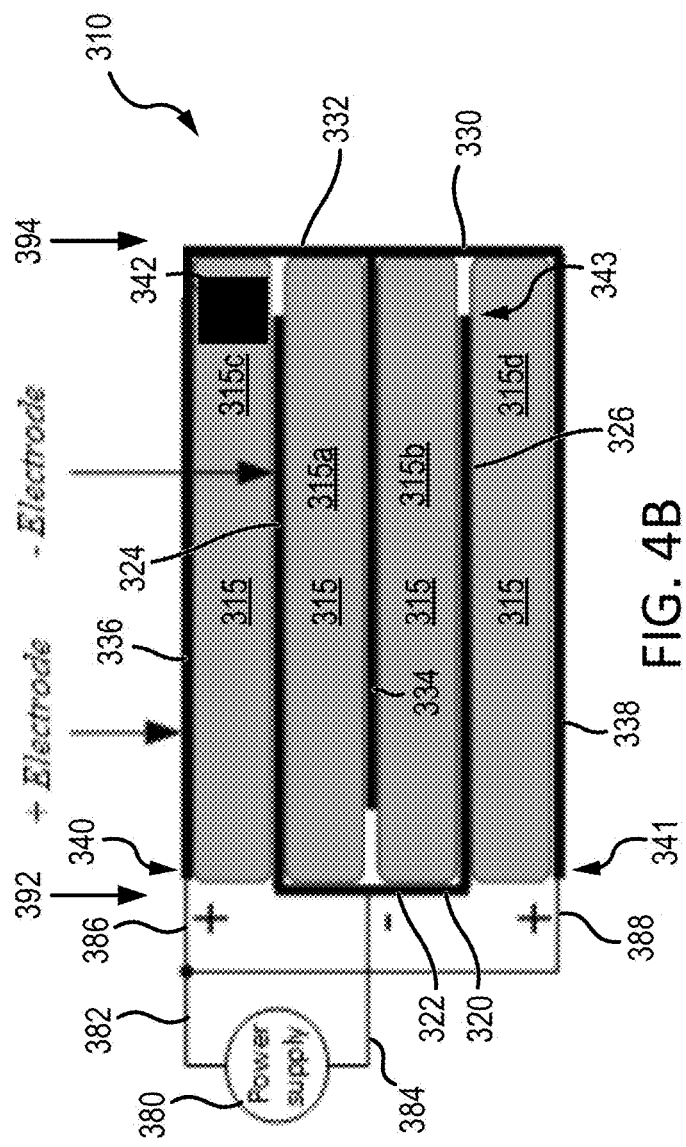
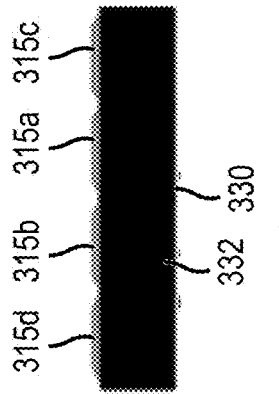
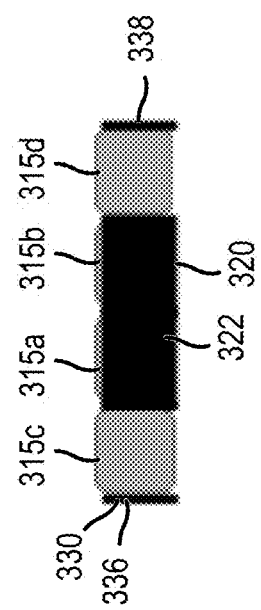
FIG. 4B
FIG. 4C
FIG. 4D

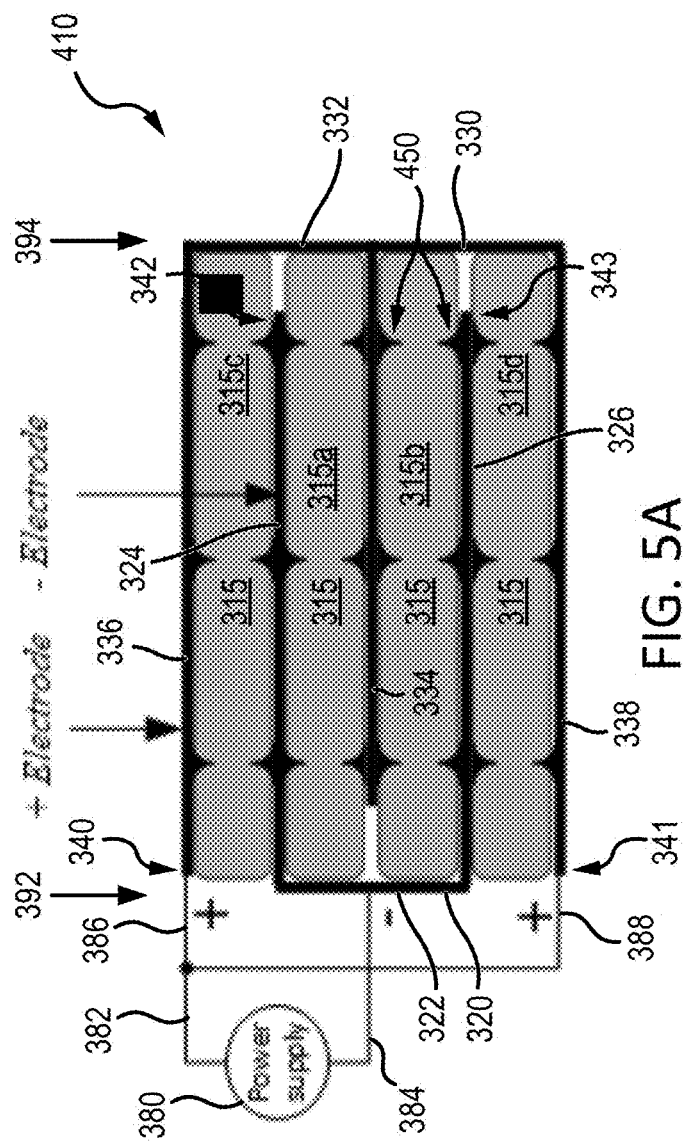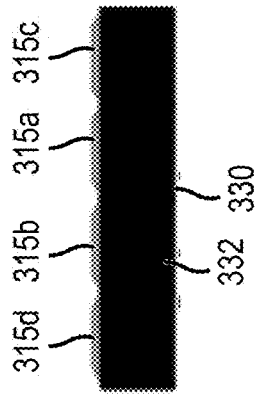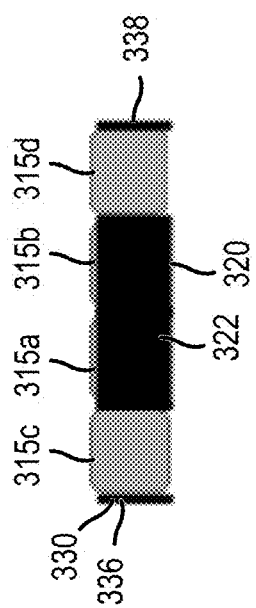

EXCIMER LAMP ELECTRODE GEOMETRY

FIELD

The present disclosure relates generally to sanitization systems and methods and, more particularly, to power supply systems and methods for ultraviolet (UV) light sanitization systems.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

An excimer lamp is disclosed, comprising a plurality of arc tubes and an electrode pair comprising a first electrode and a second electrode. The first electrode comprises a first end portion disposed at a first end of the plurality of arc tubes, a first extension extending from the first end portion, and a second extension extending from the first end portion. The second electrode comprises a second end portion disposed at a second end of the plurality of arc tubes, and a third extension extending from the second end portion, the third extension disposed between the first extension and the second extension.

In various embodiments, the plurality of arc tubes comprises a first arc tube disposed between the first extension and the second extension, and a second arc tube disposed between the first extension and the second extension, wherein the first arc tube is oriented parallel with the second arc tube.

In various embodiments, the third extension is disposed between the first arc tube and the second arc tube.

In various embodiments, the first extension is disposed opposite the first end portion from the second extension.

In various embodiments, the first extension is oriented orthogonally with respect to the first end portion, the second extension is oriented orthogonally with respect to the first end portion, and the third extension is oriented orthogonally with respect to the second end portion.

In various embodiments, the first end portion is oriented substantially parallel with the second end portion.

In various embodiments, the first extension, the second extension and the third extension are formed to extend along a tube axis direction of the plurality of arc tubes.

In various embodiments, the first extension, the second extension, and the third extension each comprise a length that is greater than half of a length of the first arc tube.

In various embodiments, the second electrode further comprises a fourth extension extending from the second end portion, and the plurality of arc tubes further comprise a third arc tube disposed between the first extension and the fourth extension.

In various embodiments, the second electrode further comprises a fifth extension extending from the second end portion, and the plurality of arc tubes further comprise a fourth arc tube disposed between the second extension and the fifth extension.

A sanitization apparatus is disclosed, comprising a power supply comprising a first positive lead, a second positive lead, and a negative lead, and an excimer lamp comprising a plurality of arc tubes and an electrode pair comprising a first electrode and a second electrode. The negative lead is coupled to the first electrode at a location substantially midway between a first end of the first electrode and a second end of the first electrode. The first positive lead is coupled to a first end of the second electrode. The second positive lead is coupled to a second end of the second electrode.

In various embodiments, the first electrode comprises a first end portion disposed at a first end of the plurality of arc tubes, a first extension extending from the first end portion, and a second extension extending from the first end portion. In various embodiments, the second electrode comprises a second end portion disposed at a second end of the plurality of arc tubes, and a third extension extending from the second end portion, the third extension disposed between the first extension and the second extension. In various embodiments, the plurality of arc tubes comprises a first arc tube disposed between the first extension and the second extension, and a second arc tube disposed between the first extension and the second extension, wherein the first arc tube is oriented parallel with the second arc tube.

In various embodiments, the negative lead is located at the first end portion.

In various embodiments, the second electrode further comprises a fourth extension extending from the second end portion. In various embodiments, the plurality of arc tubes further comprise a third arc tube disposed between the first extension and the fourth extension. In various embodiments, the second electrode further comprises a fifth extension extending from the second end portion. In various embodiments, the plurality of arc tubes further comprise a fourth arc tube disposed between the second extension and the fifth extension.

In various embodiments, the first positive lead is located at the fourth extension and the second positive lead is located at the fifth extension.

In various embodiments, each of the plurality of arc tubes comprise a noble gas sealed therein.

In various embodiments, the first electrode and the second electrode are each formed as a metal plate.

An excimer lamp is disclosed, comprising a plurality of arc tubes and a plurality of electrode plates extending along a tube axis direction of the plurality of arc tubes. Each electrode plate of the plurality of electrode plates comprises a polarity opposite that of an adjacent electrode plate. The plurality of arc tubes and the plurality of electrode plates are disposed in an alternating side-by-side orientation such that an arc tube of the plurality of arc tubes is disposed between adjacent electrode plates of the plurality of electrode plates.

In various embodiments, each electrode plate of the plurality of electrode plates is spaced apart from the adjacent electrode plate by a distance of between eighty and one hundred and twenty percent (80-120%) of a width of the arc tube disposed therebetween.

In various embodiments, each electrode plate of the plurality of electrode plates comprises a length that is between than half of a length of the arc tubes and the length of the arc tubes.

The foregoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIG. 4B, FIG. 4C, and FIG. 4D illustrate top, side, and side views of the excimer lamp of FIG. 4A, in accordance with various embodiments; and FIG. 5A, FIG. 5B, and FIG. 5C illustrate top, side, and side views of the excimer lamp having an electrode pair with edge electrode shapes, in accordance with various embodiments.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In various embodiments, Far-UVC (at or near 222 nm wavelength light) has promise to work in occupied spaces. Excimer lamps utilize a high voltage supply and have a large gas discharge.

Excimer lamp electrodes, as disclosed herein, comprise a geometry and features that tend to provide a more uniform electric field in the arc tube gas gap. Excimer lamp electrodes, as disclosed herein, comprise a geometry and features that tend to provide a more homogenous and stable dielectric barrier discharge. Excimer lamp electrodes, as disclosed herein, comprise a geometry and features that tend to provide for a desired dielectric barrier discharge at a minimal energy injection.

Figure 1:
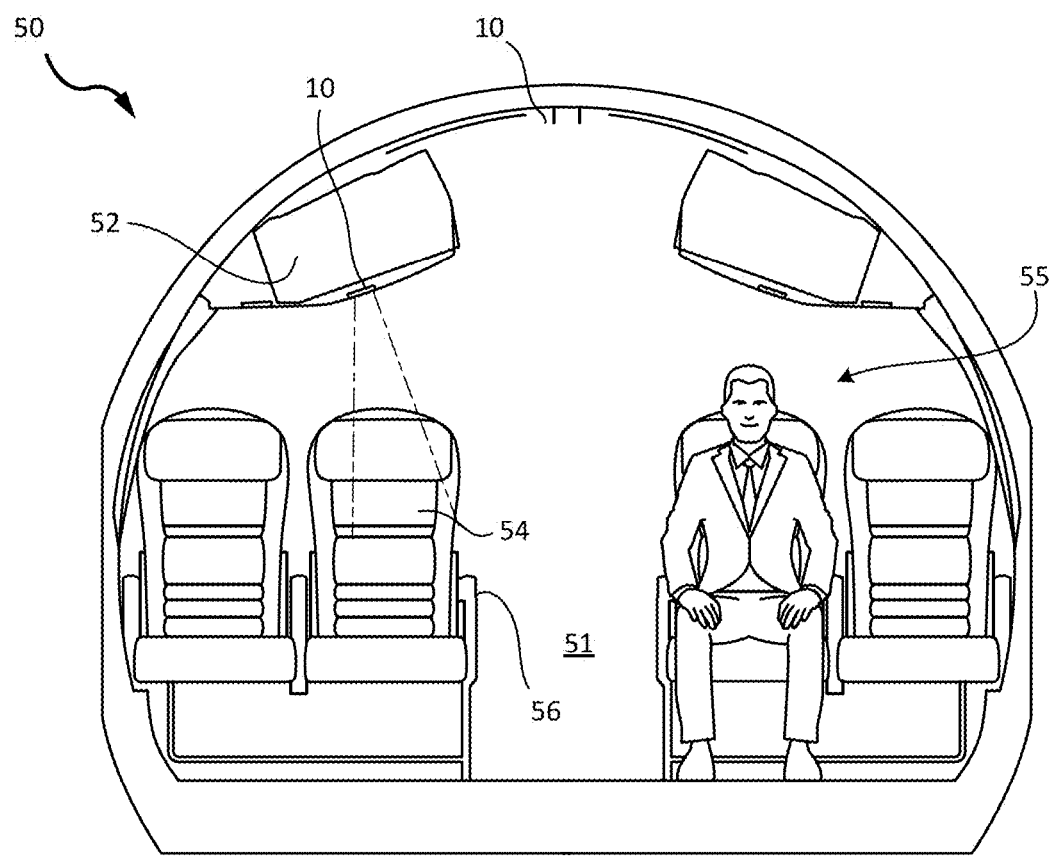
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
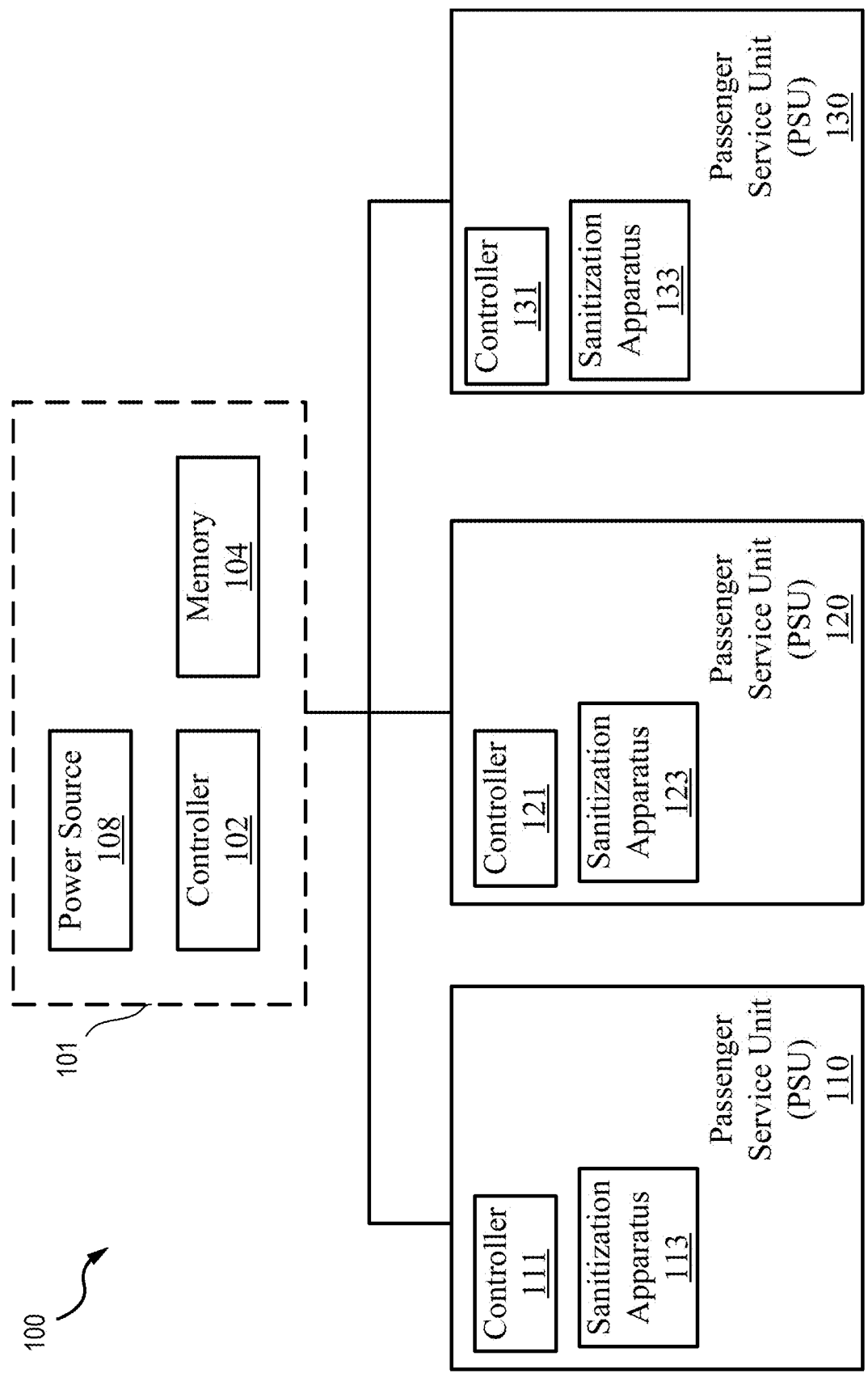
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory that is known in the art. The memory 104 may store instructions usable by the logic device to perform operations. Any appropriate computer-readable type/configuration may be utilized as the memory 104. Any appropriate data storage architecture may be utilized by the memory.

The database 104 may be integral to the control system 101 or may be located remote from the control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, performing cleaning schedules at predetermined intervals, cleaning a specific row in response to a trigger (i.e., a sneeze or the like), etc.

In various embodiments, the main control system 101 from FIG. 2 further comprises a power source 108. The power source 108 may comprise any power source known in the art, such as a battery, a solar source, an alternating current (AC) source, a direct current (DC) source, a rechargeable source, or the like.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102). For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory known in the art. The memory may store instructions usable by the logic device to perform operations. Any appropriate computer-readable type/configuration may be utilized as the memory, any appropriate data storage architecture may be utilized by the memory, or both.

In various embodiments, each PSU (e.g., PSUs 110, 120, 130) may comprise a sanitization apparatus (e.g., sanitization apparatus 113, 123, 133). As described further herein, the controller 102 may command the various local controllers (e.g., controllers 111, 121, 131) to instruct the devices therein. In various embodiments, the power source 108 is sized and configured to power all of the sanitization apparatus (e.g., sanitization apparatus 113, 123, 133) of all of the PSUs (e.g., PSUs 110, 120, 130, etc.) of sanitization system 100.

In various embodiments, each sanitization apparatus (e.g., sanitization apparatus 113, 123, 133) may be connected via digital communications, discrete communications, or wireless communications to a respective local controller (e.g., controllers 111, 121, 131).

In various embodiments, the sanitization apparatus 113 may comprise a Far-UVC light source. Sanitization apparatus 113 may comprise an excimer lamp. In various embodiments, any light source capable of outputting a light with a wavelength of about 222 nm is within the scope of this disclosure. Sanitization apparatus 113 may be configured to generate a Far-UVC light having a wavelength of between 200 and 230 nm, in accordance with various embodiments. Sanitization apparatus 113 may be configured to generate a Far-UVC light having a wavelength of between 200 and 225 nm, in accordance with various embodiments. Sanitization apparatus 113 may be configured to generate a Far-UVC light having a wavelength of between 207 and 225 nm, in accordance with various embodiments. Sanitization apparatus 113 may be configured to generate a Far-UVC light having a wavelength of about 222 nm, wherein the term "about" in this regard can only refer to a wavelength of 222 nm±15 nm. In various embodiments, the sanitization apparatus 113 is in operable communication with local controller 111 and/or a main controller 102. In this regard, in response to receiving a signal from a controller (e.g., local controller 111 and/or a main controller 102), the light source may be activated and generate Far-UVC disinfecting light.

Figure 3:
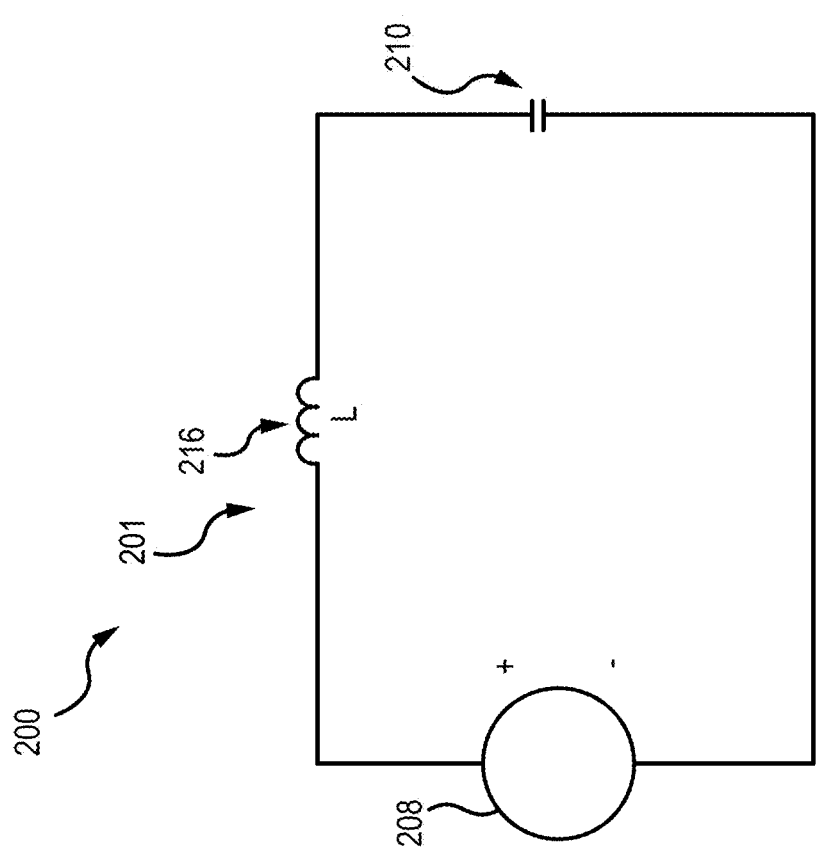
FIG. 3 illustrates a schematic view of a sanitization apparatus connected with a power source, in accordance with various embodiments.

With reference to FIG. 3, a schematic view of a sanitization apparatus 200 connected with a power source 208 is illustrated, in accordance with various embodiments. In various embodiments, sanitization apparatus 200 is similar to sanitization apparatus 113 of FIG. 2. Sanitization apparatus 200 includes an excimer lamp 210. Excimer lamp 210 is represented by, and can be modelled by, a capacitor in FIG. 3, but generally comprises two electrodes and a gas-filled cavity. In this regard, the electrical equivalent circuit of the power source and excimer lamp can be an LC resonant circuit, as illustrated in FIG. 3. Sanitization apparatus 200 includes a power supply 201 for supplying power to excimer lamp 210. Power supply may include power source 208 and inductor 216. Inductor 216 may receive an input power signal from power source 208. In various embodiments, power source 208 comprises a 24 volt DC power signal, though other voltage levels are contemplated herein, such as 12V DC, 28V DC, and 48V DC.

Figure 4A:
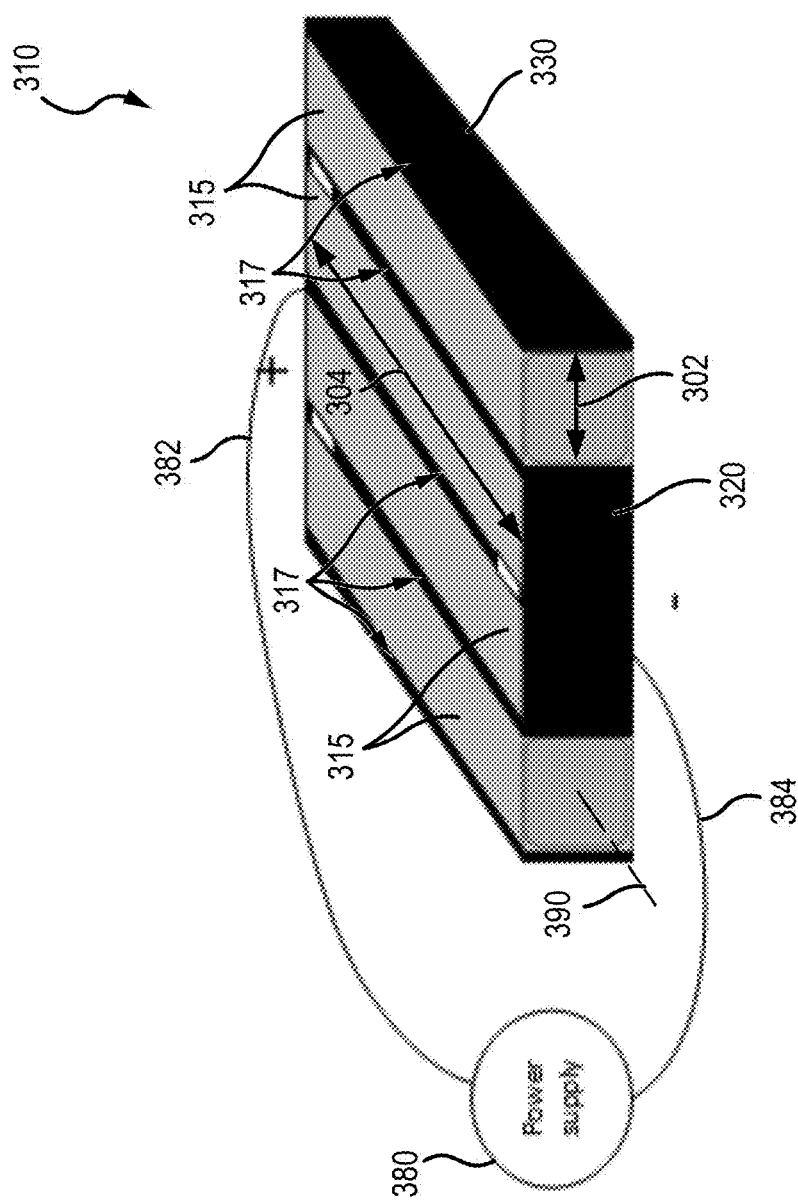
FIG. 4A illustrates a perspective view of an excimer lamp comprising a plurality of arc tubes and an electrode pair coupled with a power source, in accordance with various embodiments.

With reference to FIG. 4A, a perspective view of an excimer lamp 310 is illustrated, in accordance with various embodiments. Excimer lamp 310 includes a plurality of arc tubes 315. In various embodiments, arc tubes 315 comprise a elongated cylindrical geometry having a round cross-section. However, it is contemplated that arc tubes 315 may each comprise an elongated cylindrical geometry, an elongated square geometry with rounded corners, or any other similarly shaped elongate geometry. Arc tubes 315 may each be oriented parallel to each other. The illustrated embodiment shows 4 arc tubes 315, though excimer lamp 310 may include any suitable number of arc tubes 315, such as two, four, five, six, seven, eight, nine, ten, or more arc tubes 315.

Each of the arc tubes 315 may be made from a dielectric material. For example, ozoneless silica glass (quartz glass) or fused silica glass may be used as a material of the arc tubes 315.

A noble gas is sealed in each of the arc tubes 315. For example, the noble gas may include xenon (Xe) gas, krypton (Kr) gas, argon (Ar) gas, or neon (Ne) gas. One of these gases may be used, or a suitable combination of these gases may be used as the noble gas.

Excimer lamp 310 may further include a plurality of electrode plates 317 extending along a tube axis direction (i.e., parallel with arc tube axis 390) of the plurality of arc tubes 315. Each electrode plate 317 comprises a polarity opposite that of an adjacent electrode plate 317, as described herein. The plurality of arc tubes 315 and the plurality of electrode plates 317 are disposed in an alternating side-by-side orientation such that each arc tube 315 is disposed between adjacent electrode plates 317.

In various embodiments, each electrode plate 317 is spaced apart from immediately adjacent electrode plates 317 by a distance of between eighty and one hundred and twenty percent (80-120%) of a width 302 of the arc tube 315 disposed therebetween. In various embodiments, each electrode plate 317 is spaced apart from the immediately adjacent electrode plates 317 by a distance substantially equal to width 302.

In various embodiments, each electrode plate 317 comprises a length that is between than half of a length 304 of the arc tubes 315 and the length 304 of the arc tubes 315. In various embodiments, each electrode plate 317 comprises a length that is between eighty percent (80%) of length 304 and one hundred and five percent (105%) of the length 304. In various embodiments, one or more electrode plates 317 comprise a length that is substantially equal to length 304. Each electrode plate 317 may be formed to extend along a tube axis direction of the plurality of arc tubes 315 (i.e., parallel with arc tube axis 390).

Excimer lamp 310 may comprise an electrode pair comprising a first electrode 320 (also referred to herein as a negative electrode) and a second electrode 330 (also referred to herein as positive electrode). First electrode 320 may comprise a first polarity and second electrode 330 may comprise a second polarity. First electrode 320 is described herein as comprising a negative polarity and second electrode 330 is described herein as having a positive polarity. However, the polarity of first electrode 320 and second electrode 330 may be reversed in various embodiments without departing from the scope of the present disclosure.

A power supply 380 may be coupled to excimer lamp 310 via a positive lead 382 and a negative lead 384. In various embodiments, positive lead 382 is coupled to second electrode 330. In various embodiments, negative lead 384 is coupled to first electrode 320.

With reference to FIG. 4B, a top view of excimer lamp 310 is illustrated, in accordance with various embodiments. In various embodiments, first electrode 320 is formed as an elongated metal plate, such as a copper plate, though other electrically conductive metals are within the scope of the present disclosure. First electrode 320 may comprise an end portion 322 (also referred to herein as a first end portion) disposed at a first end 392 of the plurality of arc tubes 315. First electrode 320 may further comprise a first extension 324 extending from end portion 322. First electrode 320 may further comprise a second extension 326 extending from end portion 322. First extension 324 may be disposed opposite first end portion 322 from second extension 326. First end portion 322 may be oriented substantially orthogonal with respect to first extension 324 and second extension 326. In this regard, first end portion 322, first extension 324, and second extension 326 may be formed in a substantially "U"-shaped geometry.

In various embodiments, second electrode 330 is formed as an elongated metal plate, such as a copper plate, though other electrically conductive metals are within the scope of the present disclosure. Second electrode 330 may comprise an end portion 332 (also referred to herein as a second end portion) disposed at a second end 394 of the plurality of arc tubes 315. Second electrode 330 may further comprise a third extension 334 extending from end portion 332. End portion 332 may be oriented substantially orthogonal with respect to third extension 334.

In various embodiments, third extension 334 is disposed between first extension 324 and second extension 326. A first arc tube 315a may be disposed between the first extension 324 and the second extension 326. A second arc tube 315b may be disposed between the first extension 324 and the second extension 326.

In various embodiments, second electrode 330 further comprises a fourth extension 336 extending from end portion 332. In this regard, end portion 332, third extension 334, and fourth extension 336 may form a substantially "U"-shaped geometry. In various embodiments, first extension 324 is disposed between third extension 334 and fourth extension 336. A third arc tube 315c may be disposed between the first extension 324 and the fourth extension 336.

In various embodiments, second electrode 330 further comprises a fifth extension 338 extending from the second end portion 332. In various embodiments, fifth extension 338 is disposed opposite end portion 332 from fourth extension 336. In this regard, end portion 332, third extension 334, and fifth extension 338 may form a substantially "U"-shaped geometry. Moreover, end portion 332, fourth extension 336, and fifth extension 338 may form a substantially "U"-shaped geometry. Still further, end portion 332, third extension 334, fourth extension 336, and fifth extension 338 may form a substantially "E"-shaped geometry. A fourth arc tube 315d may be disposed between second extension 326 and fifth extension 338.

In various embodiments, positive lead 382 may comprise a first positive lead 386 and a second positive lead 388. First positive lead 386 may be attached to a first end 340 of second electrode 330. First positive lead 386 may be attached to second electrode 330 at the end 340 of fourth extension 336. Second positive lead 388 may be attached to a second end 341 of second electrode 330. Second positive lead 388 may be attached to second electrode 330 at the end 341 of fifth extension 338. Negative lead 384 may be coupled to first electrode 320 at a location substantially midway between a first end 342 of first electrode 320 and a second end 343 of first electrode 320. Negative lead 384 may be coupled to a midpoint of end portion 322. In this manner, the electric field between first electrode 320 and second electrode 330 during operation of excimer lamp 310 tends to be more evenly distributed along the longitudinal axis of arc tubes 315. By providing a single electric current return path (i.e., negative lead 384), the electric field energy may be more evenly distributed along the longitudinal axis of arc tubes 315.

First electrode 320 may be formed as a metal plate oriented vertically between each of the arc tubes 315. In this manner, substantially all of the surface area of arc tubes 315, as viewed from the top surface (see FIG. 4B), is visible. In this manner, the UV light emitted from arc tubes 315 may be unobstructed from the top surface.

With reference to FIG. 4C, a side view (i.e., the left side as shown in FIG. 4B) of the excimer lamp 310 of FIG. 4B is illustrated, in accordance with various embodiments.

With reference to FIG. 5A, FIG. 5B, and FIG. 5C, a top view, a first side view, and a second side view, respectively, of an excimer lamp 410 is illustrated, in accordance with various embodiments. With respect to FIG. 5A through FIG. 5C, elements with like element numbering, as depicted in FIG. 3A through FIG. 3D, are intended to be the same and will not necessarily be repeated for the sake of clarity. Excimer lamp 410 may be similar to excimer lamp 310 of FIG. 3A, except that first electrode 320 and second electrode 330 of excimer lamp 410 further comprise "edge electrode shapes" 450.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. An excimer lamp comprising:
   a plurality of arc tubes; and
   an electrode pair comprising a first electrode and a second electrode,
   wherein the first electrode comprises a first end portion disposed at a first end of the plurality of arc tubes, a first extension extending from the first end portion at a first extension point, and a second extension extending from the first end portion at a second extension point, wherein the first end portion of the first electrode extends between and terminates at the first extension point and the second extension point, and wherein the second electrode comprises a second end portion disposed at a second end of the plurality of arc tubes, and a third extension extending from the second end portion, the third extension disposed between the first extension and the second extension.

2. The excimer lamp of claim 1, wherein the plurality of arc tubes comprises:
   a first arc tube disposed between the first extension and the second extension; and
   a second arc tube disposed between the first extension and the second extension, wherein the first arc tube is oriented parallel with the second arc tube.

3. The excimer lamp of claim 2, wherein the third extension is disposed between the first arc tube and the second arc tube.

4. The excimer lamp of claim 3, wherein the first extension is disposed opposite the first end portion from the second extension.

5. The excimer lamp of claim 3, wherein the first extension, the second extension, and the third extension each comprise a length that is greater than half of a length of the first arc tube.

6. The excimer lamp of claim 1, wherein the first extension is oriented orthogonally with respect to the first end portion, the second extension is oriented orthogonally with respect to the first end portion, and the third extension is oriented orthogonally with respect to the second end portion.

7. The excimer lamp of claim 6, wherein the first end portion is oriented substantially parallel with the second end portion.

8. The excimer lamp of claim 1, wherein the first extension, the second extension and the third extension are formed to extend along a tube axis direction of the plurality of arc tubes.

9. The excimer lamp of claim 1, wherein the second electrode further comprises a fourth extension extending from the second end portion; and
the plurality of arc tubes further comprise a third arc tube disposed between the first extension and the fourth extension.

10. The excimer lamp of claim 9, wherein the second electrode further comprises a fifth extension extending from the second end portion; and
the plurality of arc tubes further comprise a fourth arc tube disposed between the second extension and the fifth extension.

11. A sanitization apparatus comprising:
a power supply comprising a first positive lead, a second positive lead, and a negative lead; and
an excimer lamp comprising a plurality of arc tubes and an electrode pair comprising a first electrode and a second electrode;
wherein the negative lead is coupled to the first electrode disposed on a first end of the plurality of arc tubes at a location substantially midway between a first end of the first electrode and a second end of the first electrode; and
the first positive lead is coupled to a first end of the second electrode disposed on the first end of the plurality of arc tubes; and
the second positive lead is coupled to a second end of the second electrode disposed on the first end of the plurality of arc tubes.

12. The sanitization apparatus of claim 11, wherein the first electrode comprises a first end portion disposed at the first end of the plurality of arc tubes, a first extension extending from the first end portion, and a second extension extending from the first end portion;
the second electrode comprises a second end portion disposed at a second end of the plurality of arc tubes, and a third extension extending from the second end portion, the third extension disposed between the first extension and the second extension; and
the plurality of arc tubes comprises:
a first arc tube disposed between the first extension and the second extension; and
a second arc tube disposed between the first extension and the second extension,
wherein the first arc tube is oriented parallel with the second arc tube.

13. The sanitization apparatus of claim 12, wherein the second electrode further comprises a fourth extension extending from the second end portion;
the plurality of arc tubes further comprise a third arc tube disposed between the first extension and the fourth extension;
the second electrode further comprises a fifth extension extending from the second end portion; and
the plurality of arc tubes further comprise a fourth arc tube disposed between the second extension and the fifth extension.

14. The sanitization apparatus of claim 13, wherein the first positive lead is located at the fourth extension and the second positive lead is located at the fifth extension.

15. The sanitization apparatus of claim 11, wherein each of the plurality of arc tubes comprise a noble gas sealed therein.

16. The sanitization apparatus of claim 11, wherein the first electrode and the second electrode are each formed as a metal plate.

17. An excimer lamp comprising:
a plurality of arc tubes;
a plurality of electrode plates extending along a tube axis direction of the plurality of arc tubes, wherein each electrode plate of the plurality of electrode plates comprises a polarity opposite that of an adjacent electrode plate, and wherein the plurality of arc tubes and the plurality of electrode plates are disposed in an alternating side-by-side orientation such that an arc tube of the plurality of arc tubes is disposed between adjacent electrode plates of the plurality of electrode plates;
a first end portion disposed at a first end of the plurality of arc tubes connecting alternating electrode plates of a first polarity; and
a second end portion disposed at a second end of the plurality of arc tubes connecting alternating electrode plates of a second polarity, wherein the first end portion has a width that is less than a total width of the plurality of arc tubes.

18. The excimer lamp of claim 17, wherein each electrode plate of the plurality of electrode plates is spaced apart from the adjacent electrode plate by a distance of between eighty and one hundred and twenty percent (80-120%) of a width of the arc tube disposed therebetween.

19. The excimer lamp of claim 18, wherein each electrode plate of the plurality of electrode plates comprises a length that is between half of a length of a first arc tube in the plurality of arc tubes arc tubes and the length of first arc tube.

\* \* \* \* \*